United States Patent [19]

Arms

[11] Patent Number: 4,993,428
[45] Date of Patent: Feb. 19, 1991

[54] METHOD OF AND MEANS FOR IMPLANTING A PRESSURE AND FORCE SENSING APPARATUS

[75] Inventor: Steven W. Arms, Burlington, Vt.
[73] Assignee: MicroStrain Company, Burlington, Vt.
[21] Appl. No.: 478,426
[22] Filed: Feb. 12, 1990
[51] Int. Cl.⁵ ............................................. A61B 5/103
[52] U.S. Cl. .................................................. 128/774
[58] Field of Search ................................ 128/774, 782
[56] References Cited

U.S. PATENT DOCUMENTS

| | | | |
|---|---|---|---|
| 4,204,544 | 5/1980 | Feldstein et al. | 128/774 |
| 4,294,015 | 10/1981 | Drouin et al. | 128/774 |
| 4,813,435 | 3/1989 | Arms | 128/774 |

Primary Examiner—Kyle L. Howell
Assistant Examiner—Kevin Pontius
Attorney, Agent, or Firm—Thomas N. Neiman

[57] ABSTRACT

This apparatus is adapted for replaceable implantation in soft body tissues for the measurement of the mechanical behavior of the soft tissues of the body. The apparatus consists of a thin walled tube with a piezo-resistive strain gauge element bonded to its walls. Tension in tissue fiber bundles results in a squeezing pressure against the sides of the tube, which produces a change in the shape of the tube and thus a change in the resistance of the strain gauge element. This resistance change is then measured and displayed. A method of inserting and removing the apparatus is also described, as are several techniques for calibration.

6 Claims, 2 Drawing Sheets

METHOD OF AND MEANS FOR IMPLANTING A PRESSURE AND FORCE SENSING APPARATUS

This invention pertains to medical measurement devices, and in particular to such medical measurement devices that relate to the measurement of the mechanical behavior of the soft tissues of the body by implanting a pressure and force sensing apparatus that can easily be implanted and removed as necessary.

Devices that measure the mechanical behavior of soft tissue are well known to those interested in the field of measuring the relative movement of individual parts of the body. The prior art contains many examples which pertain to measuring relative movement includes the U. S. Patent issued to Steven W. Arms for an Implantable Displacement Sensor Means, #4,813,435 issued on 21 Mar. 1989. This device measures soft tissue tension by sensing the squeezing against the sides of the device. This device was an improvement over previous devices shown in the United States Patent issued to Gilbert Drounin, #4,294,015, issued on Oct. 13, 1981 for an Extensometer and the United States Patent issued to Paul H. Brace, #4,319,236 on Mar. 9, 1982 for a Hall Effect Position Detector. The maim disadvantages of these devices are that they are not completely immersed in the soft tissue, and therefor, there can be interference from bone or overlying soft tissue structures.

The difficulties that are inherent in these designs and should be overcome include the following: large sizing of the equipment; the inability to insert the entire structures within the soft tissues; lack of the ability to use those devices during arthroscopic surgery using the cannulated design.

Clearly, it is desirable for an apparatus for measuring pressure and forces within the soft tissues of the body to be developed. It is the object of this invention, then to set forth a method of and means for imprinting a pressure and force sensing apparatus which avoids the disadvantages and limitations, above-recited, which occur in previous measuring devices. It is another object of this invention to teach a device that has a small geometry and provides a continuous readout for said means.

It is also the object of this invention to teach an apparatus for measuring the mechanical behavior of soft tissue which is simple to install and use and that will enable the surgeon to easily determine the exact placement of the apparatus in the soft tissue. Particularly, it is the object of this invention to set an implantable pressure and force sensing apparatus, for measuring the mechanical behavior of the soft tissue of the body, comprising a main guide cannulae; said main guide cannulae having an alignment slot positioned at the lower end of maid main guide cannulae; said main guide cannulae further having a direction indicator at the upper end of said cannulae; said main guide cannulae further having an inner ledge at its lower end for providing buttressing means; retractable centerline cutting and positioning means; inner tubular means comprising that fit over said retractable centerline cutting and positioning means; said tubular means having at least one sensing means attached thereto; said tubular means further having an alignment projection means located at the upper end of said inner tubular means; and said tubular means further having an enlarged tapered section at the end opposite maid upper end. Furthermore, it is the object of this invention to teach a method of implanting a pressure and force sensing apparatus, for use in medical and other applications, comprising the steps of inserting the retractable trocar within the main guide cannulae; placing the inner tubular means with the sensor attached over said retractable trocar; positioning the alignment projection of said inner tubular means in the alignment slot in said main guide cannulae; pressing said trocar and said inner tubular means at the desired position on the soft tissue; allowing said trocar and said inner tubular means to penetrate and cut maid soft tissue until reaching the desired depth for implanting the sensing element while using said main guide cannulae as a buttressing element; maintaining the proper positioning of the main guide cannulae by means of a positioning arrow at the top of said guide; removing said trocar from said main guide cannulae; and removing said main guide cannulae.

Further objects and features of this invention will become more apparent by reference to the following description taken in conjunction with the accompanying figures, in which.

Figure 1:
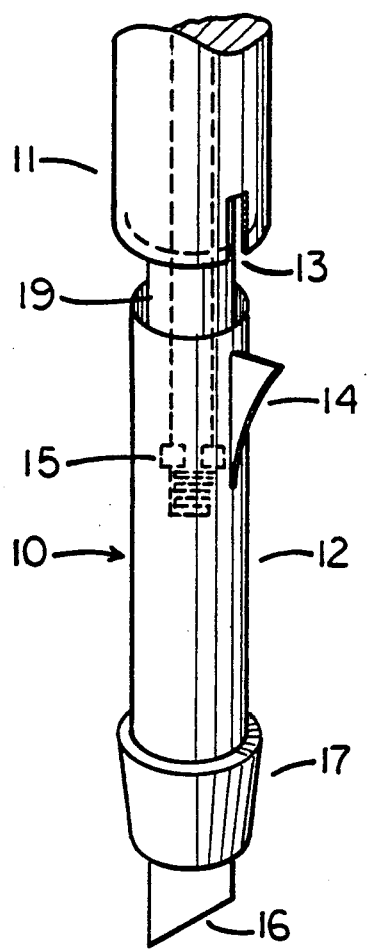
FIG. 1 is a perspective view of the novel pressure and force sensing apparatus.
Figure 2:
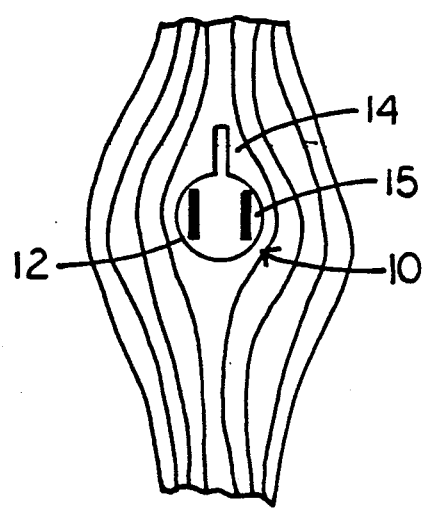
FIG. 2 is a top view of the novel apparatus in position.
Figure 3:
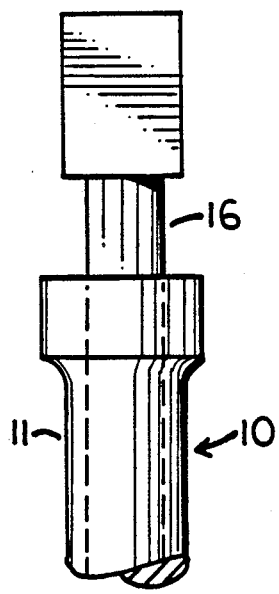
FIG. 3 is a side view of the upper end of the novel apparatus.
Figure 4:
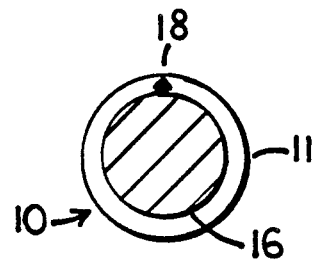
FIG. 4 is a top view.
Figure 5:
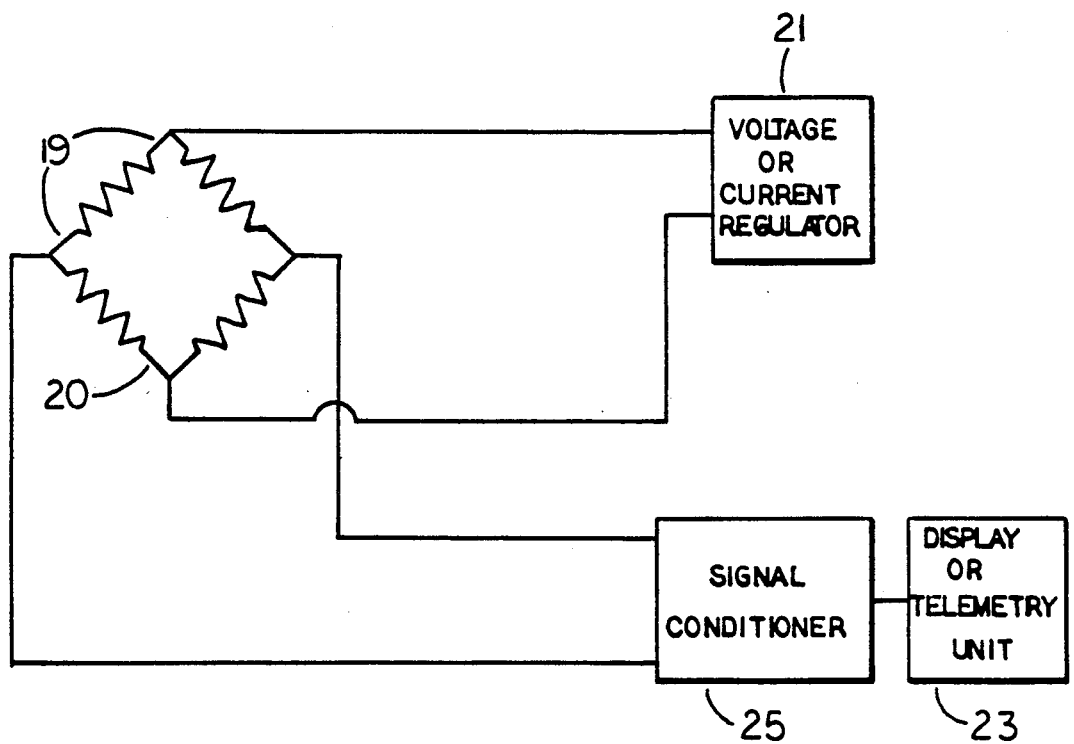
FIG. 5 is a schematic block drawing of the voltage or current regulator, bridge circuit, signal conditioner and display.

As shown in the figures, the novel pressure and force sensing apparatus 10 is comprised of main guide cannulae 11 that contains an alignment slot 13 located at the bottom end of the cannulae 11. A retractable trocar 16 fits inside the cannulae 11 and is used to cut the soft tissue during implantation. A smaller inner tube 12 fits over the trocar 16, such that the trocar can position and set the inner tube 12. Bonded to the wall of the tubing is at least one strain gauge sensor 15, which is normally a piezo-resistive type strain gauge. This sensor is wired directly to equipment that measures and displays the tension on the gauge that is caused by the squeezing of the inner tube 12 once the trocar 16 and the outer cannulae 11 are removed. A small fin 14 on the outer side of the inner tube 12 fits within the slot 13 of the main guide cannulae 11 in order to keep the inner tube 12 and the stain gauge 15 aligned as the apparatus is set in position. An inside ledge on cannulae 11 allows the main guide cannulae 11 to act as a buttress against the inner tube 12. A tapered sleeve 17 is positioned at the bottom of the inner tube 12 to prevent the apparatus from backing out the of the tissue. A guide arrow 18 at the top of the main guide cannulae 11 points out the alignment of the slot 13 and the alignment fin 14. The arrow is used during implantation to insure reproducible alignment of the apparatus. The inner tube 12 is designed to use polyimide tubing or other product that is biocompatible and strong and can be made of varying sizes for each desired purpose. Another advantage of polyimide is that it can be coated or allow metals to be bonded to it to change its physical characteristics for improved dynamic response, for altering the stiffness of the device. The circuitry is connected to the strain gauges by wired leads 19. By way of example, a wheatstone bridge 20 is comprised of an active element, that is the sensing element and a number of resistive elements that may be located external to the implantable device. Excitation of the bridge is accomplished by the use of a regulated voltage or current source 21. A change in resistance of the sensing element will produce an imbalance in the bridge which is monitored by the signal conditioner 22 and displayed by the display unit 23. An alternative embodiment would be to use an implantable telemetry device which would allow remote and untethered monitoring of data from the implanted sensor.

The novel method comprises the steps of:

inserting the retractable trocar within the main guide cannulae;

placing the inner tube with the sensor attached over the retractable trocar;

positioning the alignment projection of the inner tube in the alignment slot of the main guide cannulae;

pressing the trocar and the inner tube at the desired position of the soft tissue;

allowing the trocar and the inner tube to penetrate and cut the soft tissue until reaching the desired depth for implanting the sensing element, while being the main guide cannulae as a buttressing element;

maintaining the proper positioning of the maim guide cannulae by means of a positioning arrow at the top of the guide;

removing the trocar from said main guide cannulae; and removing the main guide cannulae.

In operation, the user can calibrate the apparatus by squeezing the sensor in a mechanical forcing frame, under known loads per unit area, and then relating the device output to a known measured input. If the user desires to measure tension, the lateral squeeze pressure must be related to tissue tension. This may be accomplished by applying known tension directly to the instrumented tissue, and relating this to the output of the apparatus. In some applications, it ia possible to apply a known external load to the bones of a joint, and thereby produce predictable loads within the instrumented tissue. This technique can be used to relate predicted loads within the instrumented soft tissue to outputs from the implanted sensor. Once the relationship has been established, subsequent outputs from the device can be used to measure ligament loading under physiologic conditions. This information can be used to evaluate knee braces, exercise programs and in the pursuit of understanding of soft tissue behavior.

While I have described my invention in connection with specific embodiments thereof, it is clearly to be understood that this is done only by way of example and not as a limitation to the scope of my invention as set forth in the objects thereof and in the appended claims.

I claim:

1. An implantable pressure and force sensing apparatus, for measuring the mechanical behavior of the soft tissue of the body, comprising:

a main guide cannulae;

said main guide cannulae having an alignment slot positioned at the lower end of said main guide cannulae;

said main guide cannulae further having a direction indicator at the upper end of said cannulae;

said main guide cannulae further having an inner ledge at its lower end for providing buttressing means;

retractable centerline cutting and positioning means;

inner tubular means comprising means that fit over said retractable centerline cutting and positioning means;

said tubular means having at least one sensing means attached thereto;

said tubular means further having an alignment projection means located at the upper end of said inner tubular means for being positioned within said alignment slot of said main guide cannulae;

said upper end of said tubular means being in replaceable contact with said buttressing means of said main guide cannulae; and said tubular means further having an enlarged tapered section at the end opposite said upper end.

2. An implantable pressure and force sensing apparatus, according to claim 1, wherein:

said sensing means comprises a piezo-resistive strain gauge means; and said strain gauge means having bonding means to allow said strain gauge means to be attached to said inner tubular means.

3. An implantable pressure and force sensing apparatus, according to claim 1, wherein:

said alignment projection comprises an extending fin on said upper portion of said inner tubular means that positions said inner tubular means and said sensing means in proper alignment by eliding into said alignment slot in said main guide cannulae.

4. An implantable pressure and force sensing apparatus, according to claim 1, wherein:

said enlarged tapered section of said inner tubular means comprises a flared base section that is wider at its uppermost end and narrower at its lower portion.

5. An implantable pressure and force sensing apparatus, according to claim 1, wherein:

said retractable centerline cutting means comprises an micro-trocar that can be withdrawn from said inner tubular means after the cut and the implantation has been made.

6. A method of implanting a pressure and force sensing apparatus into a patient's body, for use in medical and other applications, comprising the steps of:

providing a main guide cannulae which has an alignment slot formed therein;

providing a retractable trocar;

inserting the retractable trocar within the main guide cannulae;

providing an inner tubular means which has a sensing means attached thereto; and emplacing the inner tubular means over the trocar; wherein said tubular means providing step comprises providing such a tubular means which further has an alignment projection at an end thereof;

positioning the alignment projection in the alignment slot of said cannulae;

pressing the trocar and said tubular means at a desired position on the soft tissue of the patient's body;

cuttingly penetrating the soft tissue of a patient's body with said trocar and said tubular means until the desired depth, at which to implant the sensing means, has been reached; and using the cannulae as a buttressing element during the penetrating step; wherein said cannulae has a positioning arrow at one end thereof; and maintaining a proper positioning of the cannulae and the alignment projection of the tubular means by reference to the arrow;

removing the trocar from the cannulae; and removing the cannulae.

* * * * *